United States Patent [19]

Seybold

[11] 4,380,514
[45] Apr. 19, 1983

[54] PREPARATION OF OPTICAL BRIGHTENERS

[75] Inventor: Guenther Seybold, Ludwigshafen, Fed. Rep. of Germany

[73] Assignee: BASF Aktiengesellschaft, Ludwigshafen, Fed. Rep. of Germany

[21] Appl. No.: 214,227

[22] Filed: Dec. 8, 1980

[51] Int. Cl.³ ............... C07C 121/64; C07C 64/767; D06L 3/12; C11D 3/42
[52] U.S. Cl. ................ 260/465 H; 252/301.21; 260/465 D; 260/465 G; 260/465 K
[58] Field of Search ............. 252/301.21; 260/465 D, 260/465 G, 465 H, 465 K

[56] References Cited

U.S. PATENT DOCUMENTS

| | | | |
|---|---|---|---|
| 3,177,208 | 4/1965 | Stilz et al. | 260/240 |
| 3,294,570 | 12/1966 | Pommer et al. | 117/33.5 |
| 3,959,340 | 5/1976 | Weber | 260/465 K |
| 4,314,820 | 2/1982 | Weber et al. | 8/648 |
| 4,316,860 | 2/1982 | Marky | 260/513.7 |

FOREIGN PATENT DOCUMENTS

| | | |
|---|---|---|
| 23027 | 7/1980 | European Pat. Off. |
| 1122524 | 8/1962 | Fed. Rep. of Germany |
| 1134064 | 4/1963 | Fed. Rep. of Germany |
| 920988 | 3/1963 | United Kingdom |
| 929436 | 6/1963 | United Kingdom |

*Primary Examiner*—F. Edmundson
*Attorney, Agent, or Firm*—Oblon, Fisher, Spivak, McClelland & Maier

[57] ABSTRACT

A process for the preparation of unsymmetrically substituted optical brighteners of the general formula

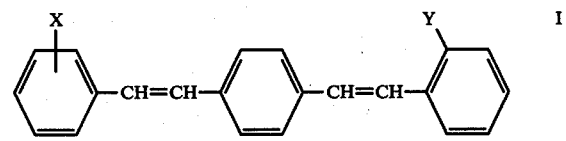

where X and Y independently of one another are hydrogen, fluorine, chlorine, cyano, $C_1$–$C_{10}$-alkoxycarbonyl, unsubstituted or substituted carbamyl or sulfamyl, a sulfonic acid aryl ester group, $C_1$–$C_{10}$-alkylsulfonyl or phenylsulfonyl, and at least one of X and Y is not hydrogen, and of mixtures of such optical brighteners, wherein terephthalaldehyde is reacted successively with a compound of the general formula IIa

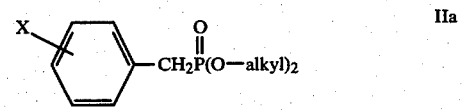

and a compound of the general formula IIb

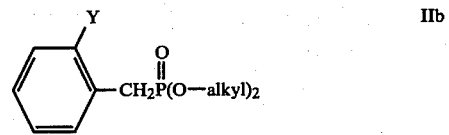

where X and Y have the above meanings and alkyl is preferably $C_1$–$C_4$-alkyl, in the presence of an alkali, in a solvent from which the monocondensation product precipitates.

7 Claims, No Drawings

PREPARATION OF OPTICAL BRIGHTENERS

The present invention relates to a process for the preparation of unsymmetrically substituted compounds of the general formula I

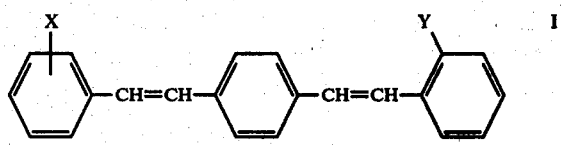

where X and Y independently of one another are hydrogen, fluorine, chlorine, cyano, $C_1$-$C_{10}$-alkoxycarbonyl, unsubstituted or substituted carbamyl or sulfamyl, a sulfonic acid aryl ester group, $C_1$-$C_{10}$-alkylsulfonyl or phenylsulfonyl, and at least one of X and Y is not hydrogen, and of mixtures of such optical brighteners, wherein terephthalaldehyde is reacted successively with a compound of the general formula IIa

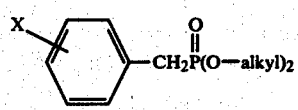

and a compound of the general formula IIb

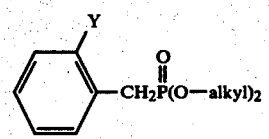

where X and Y have the above meanings and alkyl is preferably $C_1$-$C_4$-alkyl, in the presence of an alkali, in a solvent from which the monocondensation product precipitates.

Specific examples of X and Y, in addition to those already mentioned, are:

$COOCH_3$, $COOC_2H_5$, $COOC_3H_7$, $COOC_4H_9$, $COOC_6H_{13}$,

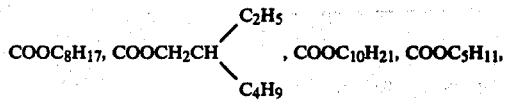

$CONHCH_3$, $CONHC_2H_5$, $CONHC_3H_7$, $CONHC_4H_9$, $CONHC_6H_{13}$, $CONHC_8H_{17}$, $CON(CH_3)_2$, $CON(C_2H_5)_2$,

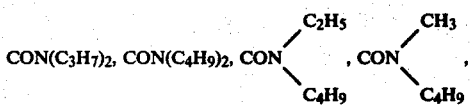

$CONHC_2H_4OH$, $CON(C_2H_4OH)_2$, $CONHC_2H_4OCH_3$,

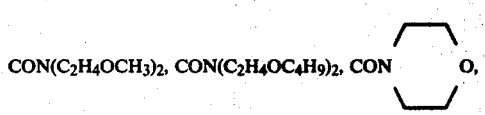

the corresponding sulfamyl radicals, $SO_2OC_6H_5$, $SO_2OC_6H_4CH_3$, $CH_3SO_2$, $SO_2C_2H_5$, $SO_2C_4H_9$, $SO_2C_{16}H_{13}$ and $SO_2C_8H_{17}$.

Suitable solvents for the reaction include, in particular, esters, ethers, hydrocarbons and chlorohydrocarbons, eg. ethyl acetate, n- and i-butyl acetate, methylglycol acetate, n- and i-propyl acetate, 1,2-dimethoxyethylene, diethylene glycol dimethyl ether, tetrahydrofuran, dioxane, toluene, xylene and chlorobenzene.

Preferred solvents are ethyl acetate, n- and i-butyl acetate, methylglycol acetate, tetrahydrofuran and dioxane.

The process according to the invention is advantageously carried out by dissolving the terephthalaldehyde in the solvent and then adding the compound of the formula IIa, followed by slow addition of the amount of alkali required for the condensation. After completion of the reaction, which can be followed by, for example, thin layer chromatography or gas chromatography, the compound of the formula IIb and the amount of alkali required for the latter are added. Advantageous reaction temperatures are from 30° to 50° C. whilst the total reaction time is as a rule from 6 to 12 hours.

Particularly suitable alkalis are alkali metal alcoholates, eg. sodium methylate, ethylate and butylate and potassium methylate, ethylate and butylate.

Details of the process according to the invention may be found in the Examples, where parts and percentages are by weight, unless stated otherwise.

Using the process according to the invention, it is possible to prepare compounds, and mixtures of compounds, of the general formula I, which do not contain any p,p'-isomers. The compounds and mixtures of compounds prepared according to the invention may be used as optical brighteners and exhibit particularly good fixing characteristics and a high brightening yield.

Mixtures of dicyano compounds, especially of o,m'-dicyano-bis-styrylbenzene and o,p'-dicyano-bis-styrylbenzene with o,o'-dicyano-bis-styrylbenzene, as well as mixtures of the o,m'- compound and o,p'- compound, are prepared. For instance, preferred mixtures are described in Examples 6, 24 and 25.

EXAMPLE 1

200 parts of 30% strength sodium methylate solution in methanol are added dropwise in the course of 4 hours to a mixture of 146 parts of 93% strength terephthalaldehyde, 275 parts of 93% strength diethyl o-cyanobenzylphosphonate and 1,200 parts of methylglycol acetate at 30°-35° C., with vigorous stirring. Stirring is continued for 4 hours at 30°-35° C. and 300 parts of 85% strength diethyl p-cyanobenzylphosphonate are then added. Thereafter, 306 parts of 30% strength sodium methylate solution are added dropwise in the course of 4 hours at 45°-50° C. Stirring is continued for 5 hours at the same temperature, the mixture is cooled to room temperature and the product is filtered off and washed thoroughly with methanol.

Yield: 260 parts of greenish yellow crystals (melting point 190°-192° C.) of the formula

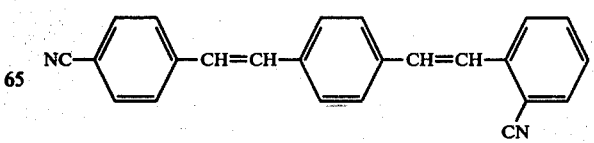

EXAMPLE 2

The procedure described in Example 1 was followed, but instead of 1,200 parts of methylglycol acetate, 1,400 parts of tetrahydrofuran were employed.

Yield of product (consisting of a single substance): 73%.

EXAMPLE 3

The procedure described in Example 1 was followed, but instead of 1,200 parts of methylglycol acetate, 1,100 parts of ethyl acetate were used.

Yield: as in Example 1.

EXAMPLE 4

The procedure followed was as in Example 1, but dioxane was used as the solvent.

Yield: 72%.

EXAMPLE 5

The procedure followed was as in Example 1, but isobutyl acetate was used as the solvent.

Yield: 78%.

EXAMPLE 6

2.34 parts of a 30% strength sodium methylate solution in methanol were added dropwise, in the course of 5 hours, to a mixture, stirred at 120 rpm, of 10 parts of methylglycol acetate, 1.4 parts of terephthalaldehyde and 3.3 parts of diethyl o-cyanobenzylphosphonate at 28°–32° C. After stirring for a further 4 hours at 40°–45° C., 1.9 parts of diethyl p-cyanobenzylphosphonate were added, and 1.7 parts of a 30% strength solution of sodium methylate in methanol were then introduced dropwise in the course of 6 hours at 35°–40° C. After stirring for a further 6 hours at 45°–50° C., the greenish white precipitate was filtered off.

Yield: 2.55 parts.

According to analysis by gas chromatography, the product is a mixture of

65% of 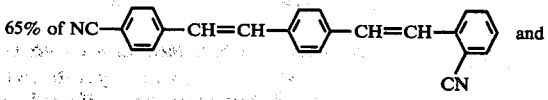 and

35% of 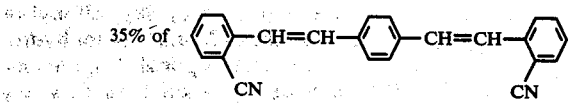

This mixture shows especially advantageous properties when used as a brightener for polyesters; in particular, its fixing capacity is exceptionally good for bis-styryl derivatives, and the brightening yield is high.

EXAMPLES 7–22

The procedure followed was similar to Example 1, except that the following solvents and phosphonates were used:

| Example | Solvent | Phosphonate ester II a | Phosphonate ester II b | Product |
|---|---|---|---|---|
| 7 | Dioxane | 2-CN-C₆H₄-CH₂P(O)(OC₂H₅)₂ | C₆H₅-CH₂P(O)(OC₂H₅)₂ | 2-NC-C₆H₄-CH=CH-C₆H₄-CH=CH-C₆H₅ |
| 8 | Ethyl acetate | 4-NC-C₆H₄-CH₂P(O)(OC₂H₅)₂ | C₆H₅-CH₂P(O)(OC₂H₅)₂ | 4-NC-C₆H₄-CH=CH-C₆H₄-CH=CH-C₆H₅ |
| 9 | " | 2-CN-C₆H₄-CH₂P(O)(OC₂H₅)₂ | 2-COOCH₃-C₆H₄-CH₂P(O)(OC₂H₅)₂ | 2-CN-C₆H₄-CH=CH-C₆H₄-CH=CH-C₆H₄-2-COOCH₃ |
| 10 | Butyl acetate | 4-NC-C₆H₄-CH₂P(O)(OC₂H₅)₂ | 2-COOC₂H₅-C₆H₄-CH₂P(O)(OC₂H₅)₂ | 4-NC-C₆H₄-CH=CH-C₆H₄-CH=CH-C₆H₄-2-COOC₂H₅ |
| 11 | " | " | 2-COOC₄H₉-C₆H₄-CH₂P(O)(OC₂H₅)₂ | 4-NC-C₆H₄-CH=CH-C₆H₄-CH=CH-C₆H₄-2-COOC₄H₉ |
| 12 | Methylglycol acetate | " | 2-Cl-C₆H₄-CH₂P(O)(OC₂H₅)₂ | 4-NC-C₆H₄-CH=CH-C₆H₄-CH=CH-C₆H₄-2-Cl |
| 13 | " | " | 2-F-C₆H₄-CH₂P(O)(OC₂H₅)₂ | 4-NC-C₆H₄-CH=CH-C₆H₄-CH=CH-C₆H₄-2-F |
| 14 | " | " | 2,4-Cl₂-C₆H₃-CH₂P(O)(OC₂H₅)₂ | 4-NC-C₆H₄-CH=CH-C₆H₄-CH=CH-C₆H₃-2,4-Cl₂ |

| Example | Solvent | Phosphonate ester II a | Phosphonate ester II b | Product |
|---|---|---|---|---|
| 15 | " | " | 2,6-dichlorophenyl-CH₂P(O)(OC₂H₅)₂ | NC-C₆H₄-CH=CH-C₆H₄-CH=CH-(2,6-dichlorophenyl) |
| 16 | Ethylglycol acetate | 2-CN-C₆H₄-CH₂P(O)(OC₂H₅)₂ | 4-(COOC₄H₉)-C₆H₄-CH₂P(O)(OC₂H₅)₂ | 2-CN-C₆H₄-CH=CH-C₆H₄-CH=CH-(2-COOC₄H₉-C₆H₄) |
| 17 | " | " | 2-Cl-C₆H₄-CH₂P(O)(OC₂H₅)₂ | 2-CN-C₆H₄-CH=CH-C₆H₄-CH=CH-(2-Cl-C₆H₄) |
| 18 | " | " | 2,4-dichlorophenyl-CH₂P(O)(OC₂H₅)₂ | 2-CN-C₆H₄-CH=CH-C₆H₄-CH=CH-(2,4-dichlorophenyl) |
| 19 | " | " | 2-F-C₆H₄-CH₂P(O)(OC₂H₅)₂ | 2-CN-C₆H₄-CH=CH-C₆H₄-CH=CH-(2-F-C₆H₄) |
| 20 | " | " | 4-CH₃-C₆H₄-CH₂P(O)(OC₂H₅)₂ | 2-CN-C₆H₄-CH=CH-C₆H₄-CH=CH-(4-CH₃-C₆H₄) |
| 21 | Tetrahydrofuran | 2-COOC₂H₅-C₆H₄-CH₂P(O)(OC₂H₅)₂ | 2-Cl-C₆H₄-CH₂P(O)(OC₂H₅)₂ | 2-COOC₂H₅-C₆H₄-CH=CH-C₆H₄-CH=CH-(2-Cl-C₆H₄) |
| 22 | " | " | 4-Cl-C₆H₄-CH₂P(O)(OC₂H₅)₂ | 2-COOC₂H₅-C₆H₄-CH=CH-C₆H₄-CH=CH-(4-Cl-C₆H₄) |

-continued

| Example | Solvent | Phosphonate ester II a | Phosphonate ester II b | Product |
|---|---|---|---|---|
| 23 | Ethylglycol acetate | ![2-CN-C6H4-CH2P(O)(OC2H5)2] | ![3-CN-C6H4-CH2P(O)(OC2H5)2] | 2-NC-C6H4-CH=CH-C6H4-CH=CH-C6H4-CN-3 |

EXAMPLE 24

20.3 parts of a 30% strength sodium methylate solution in methanol are added dropwise, in the course of 5 hours, to a mixture, stirred at 120 rpm, of 100 parts of methylglycol acetate, 14.4 parts of terephthalaldehyde and 28.6 parts of diethyl o-cyanobenzylphosphonate at 28°–32° C. The mixture is then stirred for 4 hours at 40°–45° C., 15.2 parts of diethyl m-cyanobenzyl phosphonate followed by 10.8 parts of 30% strength sodium methylate solution in methanol are then added, and the batch is stirred for 1 hour at 35° C. 6.8 parts of diethyl p-cyanobenzylphosphonate and a further 5 parts of 30% strength sodium methylate solution are then added, followed by stirring for 5 hours at 35°–40° C.

On working up the mixture as described in Example 6, a greenish white crystalline product is obtained, which according to analysis by gas chromatography contains 60% of 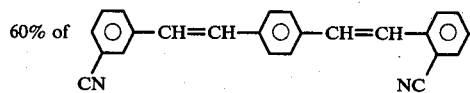

27% of 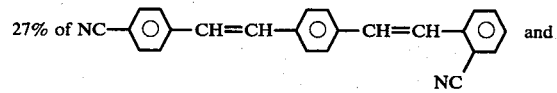 and

13% of 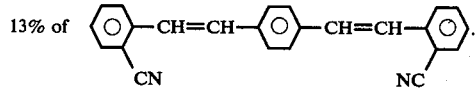.

This mixture is an excellent brightener for polyester fabrics and in particular shows good fixing properties, a reddish tint and a good brightening yield.

EXAMPLE 25

The procedure described in Example 24 is followed, 14.4 parts of terephthalaldehyde being reacted successively with 25 parts of diethyl o-cyanobenzylphosphonate, 15.2 parts of diethyl m-cyanobenzylphosphonate and 10 parts of diethyl p-cyanobenzylphosphonate. A brightener mixture containing 60% of 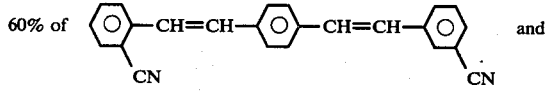 and 40% of 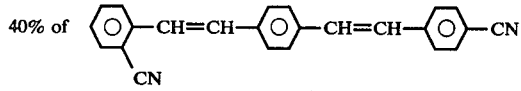

is obtained; this mixture is also an excellent brightener for polyesters.

I claim:

1. A process for the preparation of an unsymetrically substituted optical brightener compound of the general formula

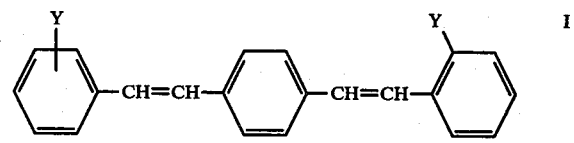

where X and Y independently of one another are hydrogen, fluorine, chlorine, cyano, $C_1$–$C_{10}$-alkoxycarbonyl, unsubstituted or substituted carbamyl or sulfamyl, a sulfonic acid aryl ester group, $C_1$–$C_{10}$-alkylsulfonyl or phenyl-sulfonyl, and at least one of X and Y is not hydrogen, and of mixtures of such optical brighteners free of p,p'-substituted compounds, which comprises reacting in a first step terephthaladehyde with a phosphonate compound of the general formula IIa

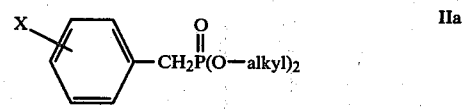

or of the general formula IIb

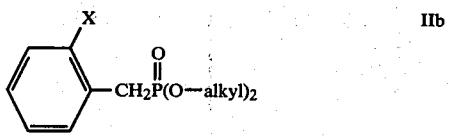

where X and Y have the above meanings in the presence of an alkali, in a solvent from which the monocondensation product of terephthaldehyde and the phosphonate compound precipitates to form a first reaction product containing the monocondensation product and thereafter completing the reaction to prepare a compound or a mixture of compounds of formula (I) by reacting the first reaction product in the presence of alkali and said solvent with a different phosphonate compound of formula IIa or IIb, with the proviso that at least one compound of formula IIa and a compound of formula IIb are reacted successively in the process.

2. A process as claimed in claim 1, wherein methylglycol acetate is used as the solvent.

3. A process as claimed in claim 1, wherein a compound or mixture of compounds in which X and Y are cyano is prepared.

4. The process as claimed in claim 1 wherein X and Y are cyano and the phosphonate compound employed in the first step is of formula IIb.

5. The process of claim 4 wherein more than one but less than two equivalents of a compound of formula IIb per mol of terephthaldehyde is employed in the first step.

6. The process of claim 1 wherein the solvent is an ester.

7. The process of claim 1 wherein the alkyl group in formulae IIa and IIb is $C_1$–$C_4$ alkyl.

UNITED STATES PATENT AND TRADEMARK OFFICE
CERTIFICATE OF CORRECTION

PATENT NO. : 4,380,514

DATED : April 19, 1983

INVENTOR(S) : GUENTHER SEYBOLD

It is certified that error appears in the above-identified patent and that said Letters Patent are hereby corrected as shown below:

On the title page the following should be added:

-- [30]   Foreign Application Priority Data

January 12, 1980   [DE] Fed. Rep. of

Germany ... 3001065--.

Signed and Sealed this

Twenty-ninth Day of November 1983

[SEAL]

Attest:

GERALD J. MOSSINGHOFF

Attesting Officer

Commissioner of Patents and Trademarks